US012639856B2

(12) United States Patent
Vatanparvar et al.

(10) Patent No.: US 12,639,856 B2
(45) Date of Patent: May 26, 2026

(54) CAMERA-BASED CONTACTLESS MONITORING OF PHYSIOLOGICAL PARAMETERS

(71) Applicant: Samsung Electronics Co., Ltd., Suwon-si (KR)

(72) Inventors: Korosh Vatanparvar, San Jose, CA (US); Jiyang Li, Hoffman Estates, IL (US); Li Zhu, Saratoga, CA (US); Migyeong Gwak, Santa Clara, CA (US); Jilong Kuang, San Jose, CA (US); Jun Gao, Menlo Park, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 346 days.

(21) Appl. No.: 18/222,118

(22) Filed: Jul. 14, 2023

(65) Prior Publication Data

US 2024/0020882 A1     Jan. 18, 2024

Related U.S. Application Data

(60) Provisional application No. 63/424,006, filed on Nov. 9, 2022, provisional application No. 63/441,096, filed
(Continued)

(51) Int. Cl.
| | |
|---|---|
| *G06K 9/00* | (2022.01) |
| *A61B 5/024* | (2006.01) |
| *A61B 5/103* | (2006.01) |
| *G06T 7/00* | (2017.01) |
| *G06T 7/246* | (2017.01) |
| *G06T 7/90* | (2017.01) |
(Continued)

(52) U.S. Cl.
CPC ............ *G06T 7/90* (2017.01); *A61B 5/02416* (2013.01); *A61B 5/1032* (2013.01); *G06T 7/0012* (2013.01); *G06T 7/246* (2017.01); *G06T 7/97* (2017.01); *G16H 40/67* (2018.01); *G16H 50/30* (2018.01); *G06T 2207/20081* (2013.01); *G06T 2207/30088* (2013.01); *G06T 2207/30168* (2013.01); *G06T 2207/30201* (2013.01)

(58) Field of Classification Search
CPC ........... G06K 9/00; G16H 40/20; A61B 5/743
USPC ........ 382/100, 103, 106–107, 128–132, 156, 382/162, 168, 173, 181, 199, 224, 254, 382/276, 286–291, 305, 312; 378/4, 21, 378/42
See application file for complete search history.

(56) References Cited

U.S. PATENT DOCUMENTS

| | | | | |
|---|---|---|---|---|
| 2019/0341147 | A1* | 11/2019 | Lord | ..................... G16H 40/20 |
| 2019/0350471 | A1* | 11/2019 | Marks | .................. A61B 5/0006 |
(Continued)

FOREIGN PATENT DOCUMENTS

| | | |
|---|---|---|
| CN | 113303776 A | 8/2021 |
| CN | 114869260 A | 8/2022 |
(Continued)

*Primary Examiner* — Seyed H Azarian

(57) ABSTRACT

In one embodiment, a method includes accessing a plurality of images of a region of interest of a person's skin and extracting, from the plurality of images, a color signal of the region of interest as a function of time. The method further includes determining, based at least on the color signal, a first quality associated with an estimated vital sign of the person, where the vital sign estimate is determined from the plurality of images.

20 Claims, 4 Drawing Sheets

Related U.S. Application Data on Jan. 25, 2023, provisional application No. 63/389,756, filed on Jul. 15, 2022, provisional application No. 63/389,720, filed on Jul. 15, 2022.

(51) Int. Cl.
_G16H 40/20_ (2018.01)
_G16H 40/67_ (2018.01)
_G16H 50/30_ (2018.01)

(56) References Cited

U.S. PATENT DOCUMENTS

| | | | |
|---|---|---|---|
| 2022/0133241 A1 | 5/2022 | Jones | |
| 2022/0301666 A1 | 9/2022 | Shluzas | |
| 2022/0343517 A1* | 10/2022 | Wang | G16H 40/67 |
| 2023/0063221 A1* | 3/2023 | Marks | A61B 5/1176 |
| 2023/0196567 A1* | 6/2023 | Aykut | G06N 3/0455 |
| | | | 382/128 |
| 2023/0363667 A1* | 11/2023 | Addison | A61B 5/743 |

FOREIGN PATENT DOCUMENTS

| | | |
|---|---|---|
| CN | 115719502 A | 2/2023 |
| WO | WO 2021-257737 A1 | 12/2021 |

* cited by examiner

CAMERA-BASED CONTACTLESS MONITORING OF PHYSIOLOGICAL PARAMETERS

PRIORITY CLAIM

This application claims the benefit under 35 U.S.C. § 119 of U.S. Provisional Patent Applications 63/389,720 filed Jul. 15, 2022; 63/389,756 filed Jul. 15, 2022; 63/424,006 filed Nov. 9, 2022; and 63/441,096 filed Jan. 25, 2023, each of which is incorporated by reference herein.

TECHNICAL FIELD

This application generally relates to camera-based contactless monitoring of physiological parameters.

BACKGROUND

Vital signs such as heart rate (HR), respiration rate (RR), oxygen saturation (SpO2), heart rate variability (HRV), blood pressure (BP), and stress index (SI), have long been considered to be important indicators of a person's health. Monitoring these vital signs has traditionally been performed by sensors that contact a person. For example, a pulse oximeter clips to a person's finger and measures the reflection or absorption of light from the person's tissue to estimate vitals including heart rate and blood oxygen levels. Measuring the amount of light absorbed or reflected by human tissues is known as photoplethysmography (PPG).

Contactless or remote sensors can also be used to measure vital signs. For example, remote PPG (rPPG) typically involves capturing images of a person's skin and determining, from these images, changes in light absorbed by or reflected from human tissue. These changes can then be related to vital signs. For example, changes in blood volume in a blood vessel caused by pressure changes due to heartbeats can influence how a given frequency of light is absorbed by the blood vessel, and these changes can be used to determine related vital signs.

DESCRIPTION OF EXAMPLE EMBODIMENTS

Remote PPG (rPPG) techniques are more convenient and less intrusive than contact-based PPG methods. For example, rPPG techniques use ubiquitous devices, such as a camera, that are commonly found in everyday environments, while contact-based methods use less common, specialized devices, such as a pulse oximeter. In addition, rPPG measurements involve capturing images of a subject, which is less intrusive and less uncomfortable than wearing a device, such as a pulse oximeter that severely limits use of the hand, or wearing a chest band. As a result, rPPG measurements can effectively be made much more frequently than PPG measurements, enabling more frequent monitoring of a person's vital signs. For example, rather than having pulse rate or blood oxygen monitored only each time a person visits a medical facility and wears a pulse oximeter, rPPG enables monitoring of pulse rate or blood oxygen (among other vital signs) as the person goes about their tasks in an environment that includes a camera for capturing images of the user, typically the user's face.

However, rPPG signals suffer from various artifacts that tend to decrease the accuracy of a resulting vital sign determination relative to a contact-based approach. For example, relative motion between a person and the detection system is much more common in rPPG, as the system is not fixed to the user, and this motion can introduce errors when using rPPG to determine a user's vital signs. In addition, changes in lighting, variations in skin properties (e.g., changes in skin coloring), and occlusion of the region of interest (e.g., face) are all problems that arise in rPPG much more frequently than they arise, if at all, in contact-based methods. There are no simple fixes for many of these problems, and some potential solutions (e.g., demanding that a person set up certain ambient lighting conditions) remove some of the benefits that rPPG has over contact-based methods.

This disclosure describes systems and methods that estimate the quality of an rPPG signal in making a vital sign determination, the quality of a vital sign estimate that is based on an rPPG signal, or both. As a result, these systems and methods provide quality indices that identify how reliable or accurate an rPPG-based vital-sign estimate is. This quality determination uses the same data (i.e., images of a region of interest) that are used to perform the rPPG determination itself. Moreover, as explained more fully herein, particular embodiments can identify a reason for a low-quality estimate, thereby providing information about changes that can be made to data acquisition to improve the fidelity of the acquired data and improve the accuracy of corresponding rPPG-based vital-sign estimates.

Figure 1:
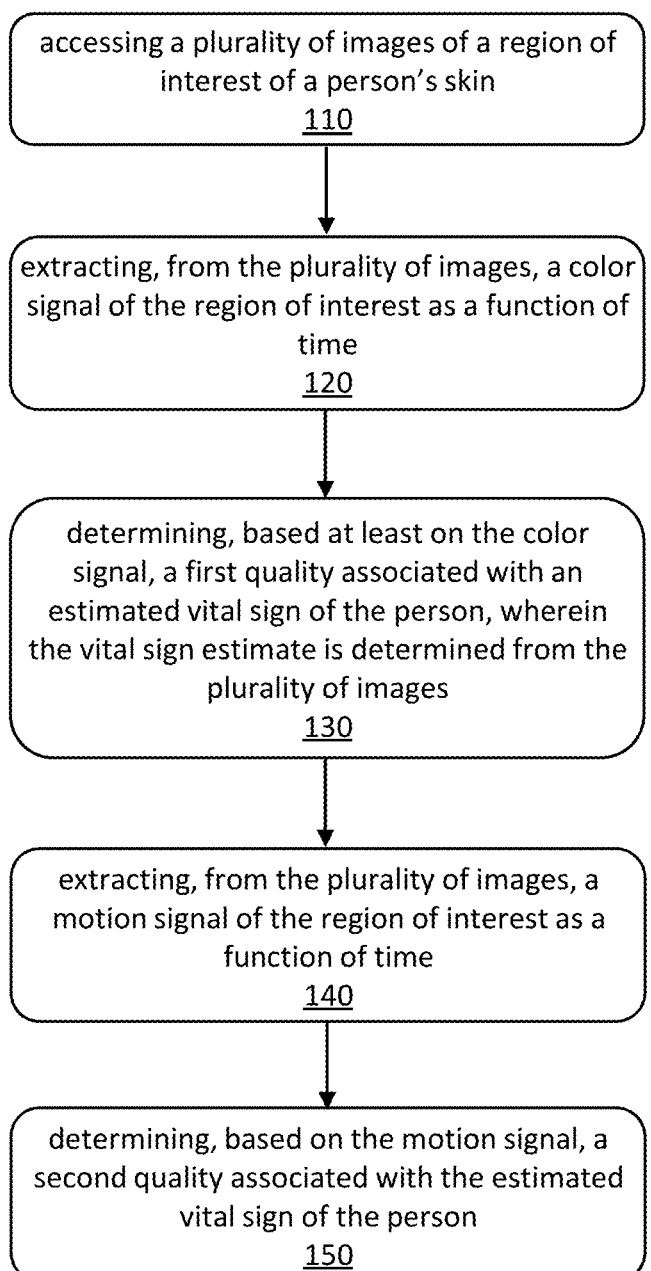
FIG. 1 illustrates an example method for estimating the quality of an estimated vital sign determined using a camera.
Figure 2:
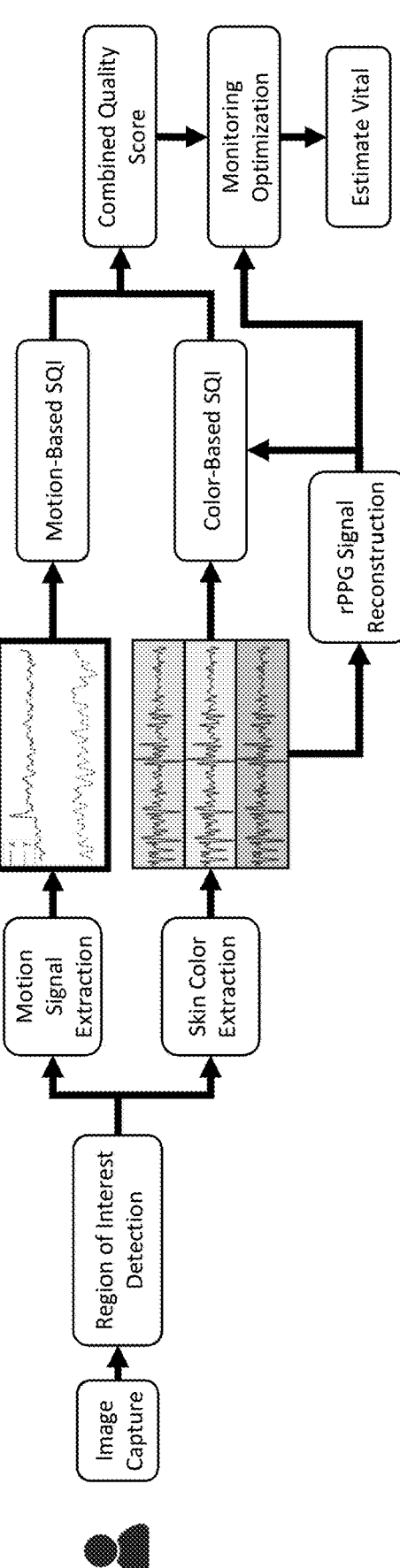
FIG. 2 illustrates an example approach for performing the example method of FIG. 1.

FIG. 1 illustrates an example method for estimating the quality of an estimated vital sign determined using a camera, as is used for rPPG. FIG. 2 illustrates, among other things, an example approach for performing the example method of FIG. 1.

Step 110 of the method of FIG. 1 includes accessing a plurality of images of a region of interest of a person's skin. The images are captured by a camera, such as a regular RGB camera or RGB plus IR camera, although in particular embodiments more than one camera may be used, as described more fully below. The plurality of images are a temporal sequence of images. For example, the images may be captured at 60 frames per second over several seconds (or longer), although this disclosure contemplates that other frame rates and other lengths of time may be used. In particular embodiments, step 110 includes accessing a subset of sequential images, i.e., accessing every nth (e.g., every other image) image from a sequence of images captured by a camera. The images may be stored on any suitable computing device, include a local computing device (e.g., on a laptop, a personal computer, a smartphone, etc.) or on a server computing device, and step 110 includes accessing or receiving the images from the device on which they are stored. In particular embodiments, a device performing some or all of the steps of FIG. 1 may also include the camera device. For example, a smartphone or a personal computer may include a camera that captures the images of the user, and that computing device may also perform the steps of the example method of FIG. 1.

In step 110, the images include a region of interest of the person's skin. In particular embodiments, this region of interest (ROI) is a person's face. As illustrated in FIG. 2, after images are captured, particular embodiments may identify the region of interest in each image. For example, a facial-recognition and segmentation algorithm may be used to identify, segment, and track the portion of the image that corresponds to the person's face in each image. In particular embodiments, a skin segmentation model may be used, e.g., in connection with the facial recognition model, to extract only skin portions of the ROI (e.g., only the skin portion of the face). In particular embodiments, each ROI may be split into a number of smaller segments, and the signal from each segment may be analyzed in separately.

The images accessed in step 110 are the same images used to estimate one or more vital signs in rPPG. The general process of estimating a vital sign using an rPPG signal is now described. First, the signal for each ROI is separated into multiple color channels, for example an R, G, and B channel, although other color formats may be used. For each color channel, the signal for each region at a given moment is averaged over the pixels in that region (i.e., the pixel intensities at a point in time are averaged over the pixels in that region). The color data is then analyzed to extract physiological signals that correspond to estimated vital signs. The green channel is often the most sensitive channel to physiological signals (e.g., the channel that best captures physiological features). Since the blue color does not penetrate much into the skin, the signal in the blue channel is more affected by motion than is the signal in the red or green channels. Meanwhile, red and green colors can further penetrate the dermis and are affected by blood volume changes (or PPG). Therefore, particular embodiments combine these colors to compensate for the common motion component of the signals and generate a cleaner single-channel rPPG signal (i.e., a reconstructed rPPG signal); however, other color combinations may be used to generated a reconstructed rPPG signal. The color signals may be converted to a chrominance color space, for example according to any of a number of well-known techniques for making such conversion, and a single-channel signal with physiological information related to blood flow may be generated.

Next, the rPPG signal is processed to extract the physiological parameter(s) of interest, such as HR, RR, SpO2, HRV, BP, or SI. The signal processing stage typically starts with cleaning the signal and filtering the portion which includes the physiological information, for example using a band-pass filter. For example, for extracting HR or SpO2, the signal can be filtered to range 0.8 Hz~3 Hz to focus on range 50 bpm~180 bpm (beats per minute). For SpO2 estimation, more than one color signal may need to be analyzed after rPPG filtering. For RR extraction, the filter can be set to range 0.08 Hz~0.75 Hz to focus on range 5 bpm~45 bpm (breaths per minute). The signal can be detrended and further smoothed over time to compensate for sudden variation and noises in the signal, which can help to remove noise due to sudden light variations and motion impacts. The cleaned and reconstructed signal may be analyzed in the frequency domain to find the most periodic component which correlates with the physiological parameter (in case of HR or RR). The cleaned and reconstructed rPPG signal can be also analyzed in the time domain to evaluate the periodicity of the signal or to extract other features for evaluating SpO2, BP, or SI.

Returning to the example method of FIG. 1, step 120 includes extracting, from the plurality of images, a color signal of the region of interest as a function of time. As explained above, the color signal may be divided into a number of channels, such as RGB channels. Each channel provides a signal for the region of interest as a function of time. For example, FIG. 2 illustrates the output of the skin color transaction block as a signal in the red (uppermost, in the figure) channel, a signal in the green (middle) channel, and a signal in the blue (bottom) channel. The signals in each of these channels may vary from each other due to the varying effects noise and biophysical interactions have on different wavelengths of light.

Figure 3:
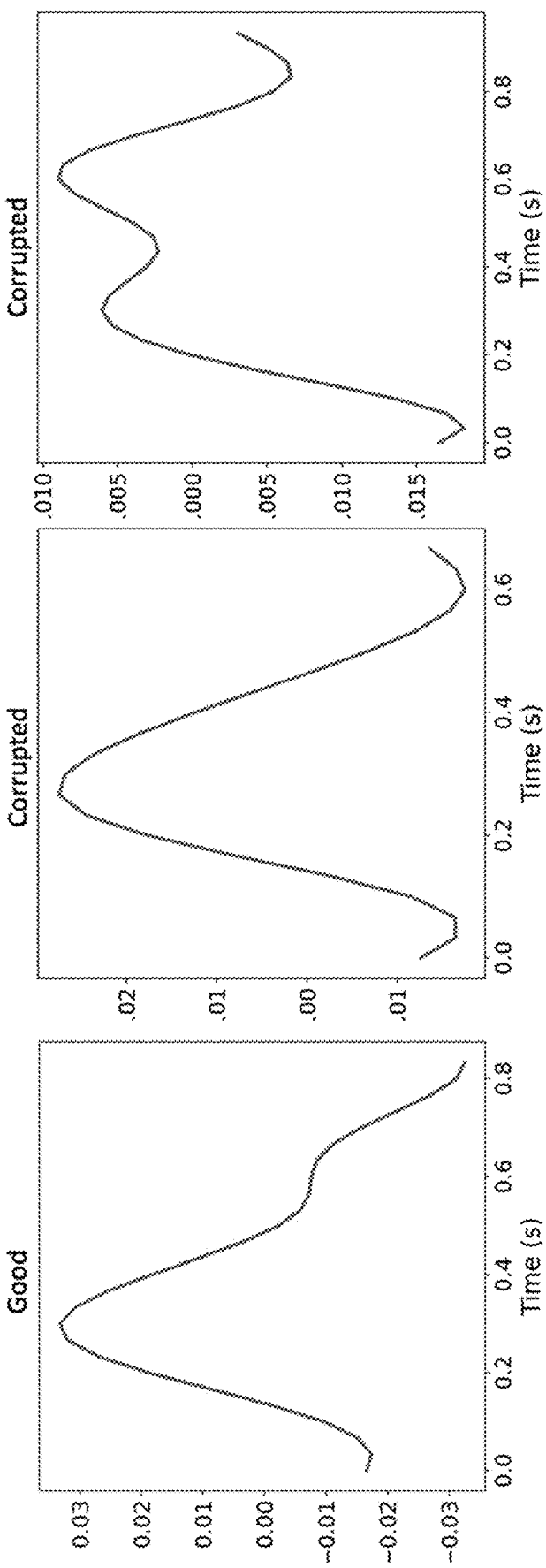
FIG. 3 illustrates examples of a good rPPG signal and two corrupted rPPG signals.

Step 130 of the example method of FIG. 1 includes determining, based at least on the color signal, a first quality associated with an estimated vital sign of the person, wherein the vital sign estimate is determined from the plurality of images. This first quality determines how accurate the vital sign estimate is or how corrupted the reconstructed rPPG signal is that is used to make that vital sign estimate. For example, FIG. 3 illustrates examples of a good rPPG signal and two corrupted rPPG signals. As illustrated in FIG. 3, the good rPPG signal contains a systolic peak and a diastolic peak. Next is shown a slightly corrupted rPPG signal that does not have a dicrotic notch. Finally, the right-most image shows a corrupted rPPG signal that includes undefined peaks in the captured signal, i.e., peaks that don't correspond to biophysical activity.

In particular embodiments, step 130 of the example method of FIG. 1 includes extracting features from the color signal, ranking the features based on rPPG quality and/or on vital-sign estimate accuracy, and determining a quality associated with the estimated vital sign. Determining a quality associated with the estimated vital sign may include determining a color-based signal quality index and/or using one or more models to estimate the accuracy of a determined vital sign.

A color signal can vary depending on how much the physiological signal is impacted by artifacts such as noise. Therefore, features in time and frequency domains can be extracted from the color signals to identify whether a signal is corrupted and correlate the signal with quality. In particular embodiments, features can be extracted from each color channel, from multiple color channels, or from a reconstructed rPPG signal. For example, a green channel correlates significantly with blood volume pulse (BVP), and therefore features from the green channel can be used to be analyze how clean a systolic peak in a signal is. As another example, signals in the blue channel and the red channel may be used to determine how other artifacts impact these channels and change the peak compared to what is observed in the green channel.

Feature extraction involves determining features for each channel of the color signal. In particular embodiments, as illustrated in the example of FIG. 2, features may also be extracted from the reconstructed rPPG signal, i.e., the reconstructed signal may be used as a fourth channel for the purposes of determining a quality of a vital-sign estimate.

Feature extraction can identify features in the time domain and in the frequency domain. For example, cardiovascular activity is represented in an rPPG signal as periodic cycles with a specific characteristic pattern in the time domain. Therefore, a subset of time-domain color features are extracted from each of the RGB channels and from the rPPG signal. For example, the following features can be extracted from the signal such as: perfusion (P), kurtosis (K), skewness (S), zero-crossing rate (Z), entropy (E), and signal-to-noise ratio (SNR). These features may be determined, respectively, as follows:

$$P = 100 \left[ (y_{max} - y_{min})/|\bar{x}| \right] \tag{1}$$

-continued $$K = 1/N \sum_{i=1}^{N} [x_i - \hat{\mu}/\sigma]^4 \qquad (2)$$

$$S = 1/N \sum_{i=1}^{N} [x_i - \hat{\mu}/\sigma]^3 \qquad (3)$$

$$E = -\sum_{i=1}^{N} x[i]^2 \; \log_e(x[i]^2) \qquad (4)$$

$$Z = 1/(N-1) \sum_{i=1}^{N} 1_{R<0}(x_i x_{i-1}) \qquad (5)$$

$$SNR = P_{signal}/P_{noise} \qquad (6)$$

However, any suitable features in the time domain may be used, including the signal average, the signal energy, the first or second derivative of the signal with respect to time, etc. In particular embodiments, several hundred features may be initially tested for each color channel, and then the features may be reduced, as discussed below, based on feature ranking.

Frequency-domain features may also be used. For example, vital signs related to respiration activity are reflected in an rPPG signal by creating specific modulations of the signal. These modulations are best captured in the frequency domain of the color signal and the reconstructed rPPG signal. The artifacts due to noise can cause changes in the values of frequency-based features, sometimes showing a dominating signal element in the range of 8~12 bpm (0.13~0.2 Hz). Any suitable frequency-based features may be extracted from a signal, including but not limited to frequency bin energy, Fourier series, signal-to-noise ratio (SNR), SNR of the $1^{st}$ or $2^{nd}$ peak, etc. As described above for time-based features, particular embodiments may use several hundred candidate frequency-based features to evaluate on each color channel and, in particular embodiments, on the reconstructed rPPG signal. In particular embodiments, combinations of features may also be used during a ranking process.

Feature ranking is established prior to runtime, so that at runtime, the system uses the ranked features for each channel. Feature ranking may occur separately for each channel, as each channel may have different features that best correlate with quality for that channel. Feature ranking may occur separately for each vital sign, as the accuracy of different vital signs correlate with different features. At runtime, these ranked features (in particular embodiments, the first n ranked features) are used to evaluate the color signal, given the vital sign of interest.

Features are ranked for a given vital sign by comparing a vital-sign estimate based on ground truth to a vital-sign estimate based on rPPG data. For example, heart-rate estimates obtained from a chest band over a period of time may be compared to heart-rate estimates from rPPG signals over that same period of time. As another example, blood oxygen data from a pulse oximeter over a period of time may be compared to blood oxygen estimates from rPPG signals over that same period of time. For each vital sign, ground truth data is obtained (e.g., using a contact-based system or other gold standard for determining that vital sign) and used to compare to the corresponding vital sign estimate from rPPG signals over that period of time.

Several approaches may be used to rank features. For example, one approach involves evaluating the features on sets of image data in which both ground-truth and rPPG estimates of a vital sign are made. When the vital-sign estimate using rPPG is significantly different than the estimate using a contact-based approach (e.g., if the difference is greater than a certain percentage, if the difference in mean absolute error is greater than a threshold, or if the difference is significant according to a statistical measure), then the corresponding rPPG data can be given one label (e.g., "noisy"). When the difference is not significant, then the data can be given a different label (e.g., clean). Each feature or combination of features can then be evaluated on the labeled data. For example, the Mann—Whitney U (MWU) test can be conducted on the feature dataset to understand how these two groups are separated with respect to each feature. A very small p-value ($\leq 0.05$) of the MWU test may be used to establish whether a particular feature is associated with the difference in noisy and clean data. In particular embodiments, each feature or combination of features may be ranked by how well that features corresponds with (i.e., is predictive of) an rPPG signal being noisy vs. clean, for the purposes of making a particular vital-sign estimate (as explained above, rPPG data may be noisy if used to estimate on vital sign (e.g., HR) but not noisy if used to estimate a different vital sign (e.g., RR)). As explained more fully below, these ranked features can then be pared to the top n features (e.g., top 10 features), which are used at runtime (e.g., used without contact-based data acquisition) to establish a quality for a particular rPPG signal or corresponding vital sign estimate obtained for a particular person.

As another example of ranking features, features and combinations of features can be input into a machine learning model along with labeled data as explained above, e.g., for noisy or clean signals. The model is trained on the input training data to output which features are predictive of an rPPG signal being clean or noisy. Any suitable machine learning model may be used, such as random forest, support vector machine, etc. The trained model is then used at runtime to estimate the likelihood that an input rPPG signal or corresponding vital-sign estimate is low quality. Based on this predicted likelihood, the input data can be rejected or weighted (e.g., weighted relatively low if the data is of low quality or weighted relatively highly if the data is of high quality). The prediction may be updated over particular time intervals, e.g., every second, every half a second, every 5 or 10 seconds, etc.

In particular embodiments, predetermined features are not established at all, and instead rPPG data and corresponding ground-truth data is input to a deep learning machine-learning model, such as a neural network. The deep-learning model outputs embedded features from the color signal that estimate the likelihood of the signal being noisy for rejecting vital outliers; in other words, the deep-learning model essentially predicts, from the training data, which aspects of the data are predicative of quality for a vital-sign estimate. The trained deep-learning model can then be used at runtime on real rPPG data to provide a quality determination for the rPPG data and/or the corresponding vital-sign estimate.

In particular embodiments, during runtime a model may evaluate the data for each subregion of a region of interest and provide a quality score for that subregion, and the scores are may then be combined (e.g., using a weighted sum).

Step 140 of the example method of FIG. 1 includes extracting, from the plurality of images, a motion signal of the region of interest as a function of time. Notably, the movement information is obtained from the same data that the color-based signal is obtained, i.e., from the same image data. In other words, a separate motion sensor (e.g., accelerometer) is not required to determine a user's motion, decreasing system complexity, and yet motion data can be used to separately evaluate the quality associated with an rPPG signal. Motion during a period of time can be due to physiological parameters (e.g., breathing, heartbeat, etc.) or due to non-physiological parameters (e.g., a user's movements).

In particular embodiments, the region of interest for motion signals may be the face or the chest. Features (e.g., landmarks) within the region of interest may be identified and tracked across image frames to determine motion (e.g., displacement in x and y axes relative to the camera sensor). For example, one motion feature may be the kurtosis level of the motion signal, which can be used to identify motion artifacts that corrupt or degrade a corresponding rPPG estimate of a vital sign.

Step 150 of the example method of FIG. 1 includes determining, based on the motion signal, a second quality associated with the estimated vital sign of the person. Candidate motion features can be predetermined in the time domain and in the frequency domain, and similar to the description above with respect to color-based feature evaluation, these candidate features may be evaluated for their predictive association with signal quality and then ranked accordingly. A signal representing motion in the x axis and a signal representing motion in the y axis may be evaluated separately with respect to the candidate features.

Candidate features for motion signals may be evaluated as described above with respect to ranking candidate features for color-based quality determinations. For example, a motion signal may be obtained from images used to generate an rPPG signal that is used to estimate a vital sign, and a contact-based approach may simultaneously be used to estimate that vital sign. Based on the difference between the rPPG estimate and the contact-based estimate, the data is divided into two different groups (e.g., noisy vs. clean), and each motion feature or combination of motion features is then evaluated with respect to its predictive association with the noisy vs. clean data. Feature evaluation may be based on a p-value associated with an MWU test or may be determined by training a machine-learning model. The features may be ranked and then pared for use during runtime. In particular embodiments, a deep-learning approach may be used to determine aspects of motion signals that correspond to low-quality rPPG data or vital-sign estimates, as described above for color-based quality determinations.

Particular embodiments may repeat one or more steps of the method of FIG. 1, where appropriate. Although this disclosure describes and illustrates particular steps of the method of FIG. 1 as occurring in a particular order, this disclosure contemplates any suitable steps of the method of FIG. 1 occurring in any suitable order. Moreover, although this disclosure describes and illustrates particular components, devices, or systems carrying out particular steps of the method of FIG. 1, such as the computer system of FIG. 4, this disclosure contemplates any suitable combination of any suitable components, devices, or systems carrying out any suitable steps of the method of FIG. 1. Moreover, this disclosure contemplates that some or all of the computing operations described herein, including the steps of the example method illustrated in FIG. 1, may be performed by circuitry of a computing device, for example the computing device of FIG. 4, by a processor coupled to non-transitory computer readable storage media, or any suitable combination thereof.

In particular embodiments, color features and motion features obtained from color signals and motion signals, respectively, from a sequence of images of an ROI may be used together to determine a quality score for an rPPG signal determined from those images and/or for a vital sign estimated from that rPPG signal. Different vital sign estimates may correspond to different input features. For example, for a heart-rate estimate, there is often a correlation between head motion features and error in the estimated heart-rate value. Likewise, there is often a correlation between signal-to-noise ratio features in one or more color channels and error in an estimated heart-rate value. Therefore, combining these two features can be used to identify errors in an estimated heart-rate value.

As explained above with respect to color features and motion features, combinations of candidate color features and motion features can be evaluated based on a comparison of rPPG-estimated vital signs and corresponding ground truth for those vital signs. For example, combination of features may be input into a machine learning model (e.g., random forest, support vector machine, etc.) with rPPG-based vital sign estimates that are labelled based on comparison with ground-truth estimates (e.g., labeled with "noisy" or "clean" class values). After training, the trained machine-learning model is used at runtime to evaluate and classify a quality of an rPPG signal and/or associated vital-sign estimated. The classification may be binary (e.g., 0 and 1 for noisy vs. clean) or may represent a probability (e.g., a value between 0 and 1) of the signal being noisy vs clean, which corresponds to the likelihood of the signal being corrupted and the estimate being unreliable. In particular embodiments, this likelihood may be combined with motion-based quality determinations and color-based quality determinations to arrive at a combined quality score.

In particular embodiments, combining motion and color features also provides information about the possible causes of signal-quality degradation. For example, if a person moves while images are being acquired, this movement will be captured in both the motion signal and also in the color signal (e.g., due to changes in lighting on ROI(s) due to the movement, etc.). One or both of these changes may result in features that indicate an rPPG signal is unreliable, and using motion features and color features together can be used to determine the cause of a corrupted rPPG signal and corresponding inaccurate vital sign estimate. These causes may be surfaced to a user or to another person (e.g., a medical professional during a telehealth appointment) in the form of notifications and/or recommendations in order to improve data capture and corresponding vital-sign estimates. For example, if a quality based on combined motion and color features is below a particular threshold value (e.g., below 0.8), then a recommendation process may evaluate whether a motion-based quality determination is below a motion-specific threshold value. If yes, then motion may be determined to be the cause of the relatively low quality, and a corresponding recommendation (e.g., "Please attempt to be stationary" or "hold still for at least 30 seconds") may be provided, for example by an audio or visual notification from a computing device. If the motion-based threshold is above the corresponding threshold, then a color-based quality determination may be compared to a color-specific threshold value. If the color-based quality determination is below the color-specific threshold value, then a corresponding recommendation (e.g., "Inadequate physiological signal, maybe due to light variation" or "increase the ambient lighting") may be provided. If both the motion-specific quality and the color-specific quality are above their corresponding thresholds, then a notification may be provided that a cause for the relatively low signal quality (as determined by the combined motion and color features) cannot be determined, and possible causes to investigate may be provided (e.g., "Inadequate physiological signal, maybe due to face occlusion or make up").

In particular embodiments, the combined motion and color quality determinations may be stored in association with a vital-sign estimate, along with individual motion-based quality determinations and color-based quality determinations. These values can then be analyzed after the fact, for example to provide context to a medical provider reviewing a patient's historical estimated vital-sign data.

Vital sign estimates made using rPPG signals can be determined by processing windows of rPPG data (e.g., a 30-second window corresponding to the most recently collected 30 seconds of data). The window may be updated periodically (e.g., every 1 second, the past 30 seconds of data may be used to estimate a vital sign). Estimates can be made by evaluating the rPPG signal during the window in either the time domain or in the frequency domain, or both. Using a relatively longer window can improve signal fidelity, for example by increasing the frequency resolution in the FFT and representing the frequency components more accurately. Thus, the influence of short-duration low-energy noise artifacts on the rPPG signal can be mitigated. However, longer windows introduce larger delays in signal processing and vital calculation. The delay may not be acceptable for the user in real-life scenarios. In another case, noise artifacts can dominate the physiological component in the rPPG signal, where the peak in the FFT spectrum does not correspond to the HR/RR. As a result, the predicted HR/RR may have great errors, and it takes longer time to recover from the error if window sizes are larger.

Particular embodiments use combined motion and color features to dynamically optimize the trade-off between rPPG quality and processing time as a result of rPPG window size. For example, instead of using a single window for vital calculation, multiple consecutive rPPG sub windows are analyzed by the vital tracker. For example, with a moving window approach, an rPPG signal of 15 s may be segmented into shorter sub windows of 5 s each, with a step size of 1 s (creating 11 sub windows in the 15 seconds window). Each of the 5-second sub windows is separately analyzed to estimate a vital sign corresponding to the data in that window. In addition, a quality score based on combined motion and color features, and corresponding artifact identification, may be performed separately for each sub window. Artifacts from each sub window may be identified and removed, or the signal from each sub window may be weighted based on its quality. In particular embodiments, the data or estimate from a particular sub window may be dropped (i.e., given a weight of 0) or kept based on the corresponding quality and/or artifact identification. While the disclosure above provides an example using 5-second sub windows, this disclosure contemplates that any suitable sub window duration may be used (e.g., a 10-second sub window, etc.).

The underlying signals and/or vital-sign estimates may then be aggregated from each sub window to arrive at a final signal and estimate, respectively. For example, a final estimated vital sign can be calculated based on the combination of the sub window estimates; for example, by taking the median of the values or taking weighted average using the quality scores as the weights. As another example, the rPPG signal of each sub window can be aggregated (for example, weighted) to generate an enhanced rPPG signal. In particular embodiments, the aggregated vital-sign estimates or rPPG signals are taken only from sub windows that are not dropped due to their quality scores or artifact identifications.

By relying on shorter sub windows, the impact of noise artifacts is isolated to a shorter duration. Multiple vital values extracted from the sub windows provide enough redundancy to compensate for the vital measurement error for shorter windows.

In particular embodiments, a duration of the sub window and thresholds for artifact removal can be tuned at runtime based on context such as the use case. The image-capture duty cycle can also be tuned. For example, during an active, spot-check scenario, a user may be instructed to stay stationary, and as a result sub window time may be increased, and the quality thresholds may be less strict (i.e., less data or vital-sign estimates will be deemed outliers and discarded or lowly weighted). On the other hand, during a passive tracking scenario in which image data is acquired while the user may be doing other tasks and is not expected to be still or have any awareness or attention to data collection, then shorter sub windows and stricter thresholds may be used. While more data will excluded or downweighed, the shorter sub windows allow the system to recover from any resulting artifact relatively more quickly.

In particular embodiments, a system may use more than one camera to capture a sequence of images of a region of interest, for example the user's face. Motion and color signal extraction and quality scores can be determined for the data from each camera. In particular embodiments, the highest quality data over a given period of time can be used to make a vital sign estimate, i.e., the quality scores can be used to select the camera that is providing the most reliable data from the perspective of rPPG analysis. Because different features are associated with different vital signs, in particular embodiments data from different cameras may be selected to provide different vital sign estimates (e.g., one camera may be providing images that are best suited to determining heart rate, while at the same time a different camera is providing images best suited to determining oxygen saturation).

The systems and methods described herein may be used to improve the vital-sign determinations made using rPPG, for example estimates based on images captured by a user's devices (e.g., smartphone, TV, smart assistants, etc.) as the user goes about their daily activities. The data may also be used by medical professionals, for example by acquiring data during telehealth visits to remotely determine and evaluate a user's vital signs, or by reviewing data captured over time to understand the user's vital-sign estimates, the associated quality, and any potential reasons for inaccurate determinations. As another example, the system and methods described herein may be used to more accurately understand users' reactions (e.g., as determined based on rPPG) signals to content, such as to video content, and content may be recommended to a user based such determinations, or particularly interesting highlights (e.g., of a video, of a video game, of a video call, etc.) corresponding to a user's reaction may be captured and made available to the user. As another example, a workout program may be adjusted in real-time based determinations of the user's physiological signals.

Figure 4:
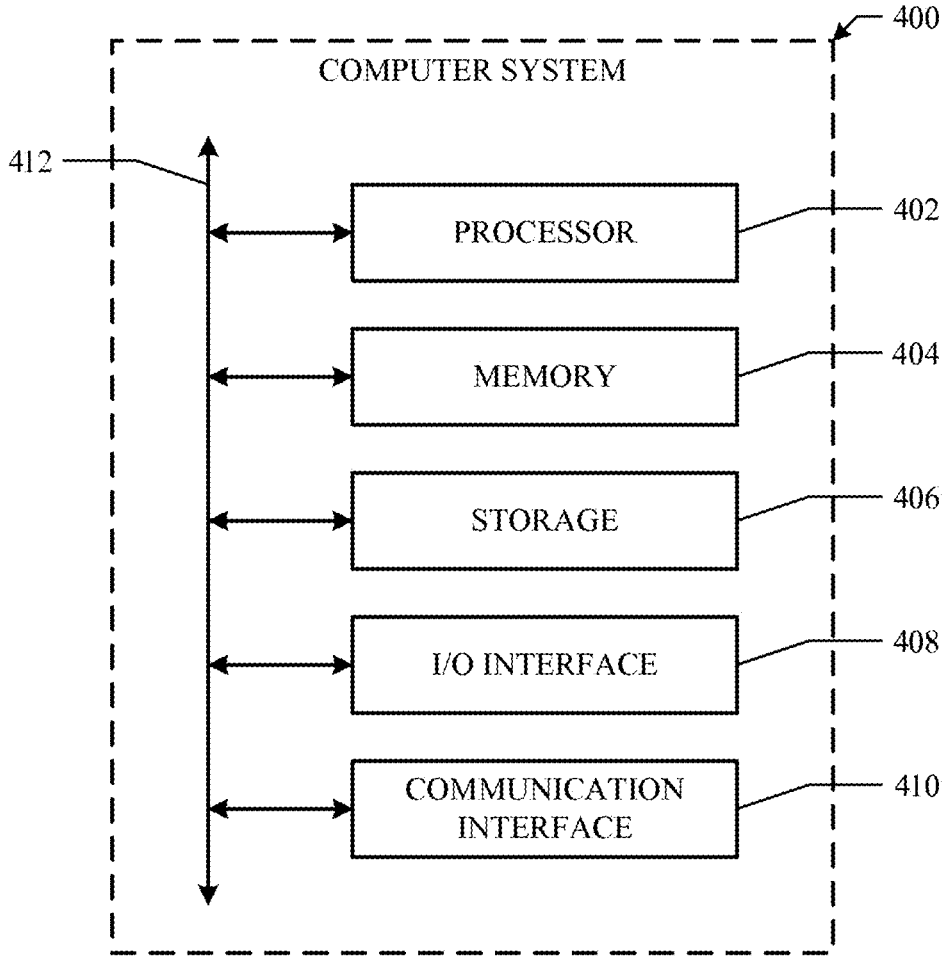
FIG. 4 illustrates an example computing system.

FIG. 4 illustrates an example computer system 400. In particular embodiments, one or more computer systems 400 perform one or more steps of one or more methods described or illustrated herein. In particular embodiments, one or more computer systems 400 provide functionality described or illustrated herein. In particular embodiments, software running on one or more computer systems 400 performs one or more steps of one or more methods described or illustrated herein or provides functionality described or illustrated herein. Particular embodiments include one or more portions of one or more computer systems 400. Herein, reference to a computer system may encompass a computing device, and vice versa, where appropriate. Moreover, reference to a computer system may encompass one or more computer systems, where appropriate.

This disclosure contemplates any suitable number of computer systems 400. This disclosure contemplates computer system 400 taking any suitable physical form. As example and not by way of limitation, computer system 400 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 400 may include one or more computer systems 400; be unitary or distributed; span multiple locations; span multiple machines; span multiple data centers; or reside in a cloud, which may include one or more cloud components in one or more networks. Where appropriate, one or more computer systems 400 may perform without substantial spatial or temporal limitation one or more steps of one or more methods described or illustrated herein. As an example and not by way of limitation, one or more computer systems 400 may perform in real time or in batch mode one or more steps of one or more methods described or illustrated herein. One or more computer systems 400 may perform at different times or at different locations one or more steps of one or more methods described or illustrated herein, where appropriate.

In particular embodiments, computer system 400 includes a processor 402, memory 404, storage 406, an input/output (I/O) interface 408, a communication interface 410, and a bus 412. Although this disclosure describes and illustrates a particular computer system having a particular number of particular components in a particular arrangement, this disclosure contemplates any suitable computer system having any suitable number of any suitable components in any suitable arrangement.

In particular embodiments, processor 402 includes hardware for executing instructions, such as those making up a computer program. As an example and not by way of limitation, to execute instructions, processor 402 may retrieve (or fetch) the instructions from an internal register, an internal cache, memory 404, or storage 406; decode and execute them; and then write one or more results to an internal register, an internal cache, memory 404, or storage 406. In particular embodiments, processor 402 may include one or more internal caches for data, instructions, or addresses. This disclosure contemplates processor 402 including any suitable number of any suitable internal caches, where appropriate. As an example and not by way of limitation, processor 402 may include one or more instruction caches, one or more data caches, and one or more translation lookaside buffers (TLBs). Instructions in the instruction caches may be copies of instructions in memory 404 or storage 406, and the instruction caches may speed up retrieval of those instructions by processor 402. Data in the data caches may be copies of data in memory 404 or storage 406 for instructions executing at processor 402 to operate on; the results of previous instructions executed at processor 402 for access by subsequent instructions executing at processor 402 or for writing to memory 404 or storage 406; or other suitable data. The data caches may speed up read or write operations by processor 402. The TLBs may speed up virtual-address translation for processor 402. In particular embodiments, processor 402 may include one or more internal registers for data, instructions, or addresses. This disclosure contemplates processor 402 including any suitable number of any suitable internal registers, where appropriate. Where appropriate, processor 402 may include one or more arithmetic logic units (ALUs); be a multi-core processor; or include one or more processors 402. Although this disclosure describes and illustrates a particular processor, this disclosure contemplates any suitable processor.

In particular embodiments, memory 404 includes main memory for storing instructions for processor 402 to execute or data for processor 402 to operate on. As an example and not by way of limitation, computer system 400 may load instructions from storage 406 or another source (such as, for example, another computer system 400) to memory 404. Processor 402 may then load the instructions from memory 404 to an internal register or internal cache. To execute the instructions, processor 402 may retrieve the instructions from the internal register or internal cache and decode them. During or after execution of the instructions, processor 402 may write one or more results (which may be intermediate or final results) to the internal register or internal cache. Processor 402 may then write one or more of those results to memory 404. In particular embodiments, processor 402 executes only instructions in one or more internal registers or internal caches or in memory 404 (as opposed to storage 406 or elsewhere) and operates only on data in one or more internal registers or internal caches or in memory 404 (as opposed to storage 406 or elsewhere). One or more memory buses (which may each include an address bus and a data bus) may couple processor 402 to memory 404. Bus 412 may include one or more memory buses, as described below. In particular embodiments, one or more memory management units (MMUs) reside between processor 402 and memory 404 and facilitate accesses to memory 404 requested by processor 402. In particular embodiments, memory 404 includes random access memory (RAM). This RAM may be volatile memory, where appropriate Where appropriate, this RAM may be dynamic RAM (DRAM) or static RAM (SRAM). Moreover, where appropriate, this RAM may be single-ported or multi-ported RAM. This disclosure contemplates any suitable RAM. Memory 404 may include one or more memories 404, where appropriate. Although this disclosure describes and illustrates particular memory, this disclosure contemplates any suitable memory.

In particular embodiments, storage 406 includes mass storage for data or instructions. As an example and not by way of limitation, storage 406 may include a hard disk drive (HDD), a floppy disk drive, flash memory, an optical disc, a magneto-optical disc, magnetic tape, or a Universal Serial Bus (USB) drive or a combination of two or more of these. Storage 406 may include removable or non-removable (or fixed) media, where appropriate. Storage 406 may be internal or external to computer system 400, where appropriate. In particular embodiments, storage 406 is non-volatile, solid-state memory. In particular embodiments, storage 406 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 406 taking any suitable physical form. Storage 406 may include one or more storage control units facilitating communication between processor 402 and storage 406, where appropriate. Where appropriate, storage 406 may include one or more storages 406. Although this disclosure describes and illustrates particular storage, this disclosure contemplates any suitable storage.

In particular embodiments, I/O interface 408 includes hardware, software, or both, providing one or more interfaces for communication between computer system 400 and one or more I/O devices. Computer system 400 may include one or more of these I/O devices, where appropriate. One or more of these I/O devices may enable communication between a person and computer system 400. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 408 for them. Where appropriate, I/O interface 408 may include one or more device or software drivers enabling processor 402 to drive one or more of these I/O devices. I/O interface 408 may include one or more I/O interfaces 408, where appropriate. Although this disclosure describes and illustrates a particular I/O interface, this disclosure contemplates any suitable I/O interface.

In particular embodiments, communication interface 410 includes hardware, software, or both providing one or more interfaces for communication (such as, for example, packet-based communication) between computer system 400 and one or more other computer systems 400 or one or more networks. As an example and not by way of limitation, communication interface 410 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 410 for it. As an example and not by way of limitation, computer system 400 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 400 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 400 may include any suitable communication interface 410 for any of these networks, where appropriate. Communication interface 410 may include one or more communication interfaces 410, where appropriate. Although this disclosure describes and illustrates a particular communication interface, this disclosure contemplates any suitable communication interface.

In particular embodiments, bus 412 includes hardware, software, or both coupling components of computer system 400 to each other. As an example and not by way of limitation, bus 412 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 412 may include one or more buses 412, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend.

What is claimed is:

1. A method comprising:
capturing, by a camera, a plurality of images of a region of interest of a person's skin;
accessing the plurality of images of the region of interest of the person's skin;
extracting, from the plurality of images, a color signal of the region of interest as a function of time;
determining, based on the color signal of the region of interest extracted from the plurality of images, a remote photoplethysmography (rPPG)-based estimate of a vital sign of the person; and
determining, based at least on the color signal, a first quality associated with the estimated vital sign of the person, wherein the first quality identifies an accuracy of the rPPG-based estimate of the vital sign using at least a subset of the same plurality of images of the region of interest that is used to perform the rPPG-based estimate of the vital sign.

2. The method of claim 1, wherein the region of interest comprises the person's face.

3. The method of claim 1, wherein extracting a color signal of the region of interest as a function of time comprises extracting, from the plurality of images, a signal as a function of time in each of a plurality of color channels.

4. The method of claim 1, wherein determining the first quality associated with the estimated vital sign of the person comprises determining the first quality based on a set of predetermined, ranked features associated with the color signal and specific to the vital sign.

5. The method of claim 1, wherein determining the first quality associated with the estimated vital sign of the person comprises:

provicing the color signal to a trained machine-learning model, wherein the trained machine learning model is trained on (1) a set of predetermined features associated with a set of color signals, (2) a set of vital sign estimates, each vital sign estimate based on one of the color signals in the set of color signals, and (3) a ground-truth vital sign estimate, each ground-truth vital sign estimate corresponding in time with a vital sign estimate from the set of vital sign estimates; and receiving, from the trained machine learning model, a quality metric for the estimated vital sign of the person.

6. The method of claim 1, further comprising:

extracting, from the plurality of images, a motion signal of the region of interest as a function of time;

determining, based on the motion signal, a second quality associated with the estimated vital sign of the person, wherein the second quality identifies a second accuracy of the rPPG-based estimate of the vital sign using at least a subset of the same plurality of images of the region of interest that is used to perform the rPPG-based estimate of the vital sign.

7. The method of claim 6, wherein determining the second quality associated with the estimated vital sign of the person comprises determining the second quality based on a set of predetermined, ranked features associated with the motion signal and specific to the vital sign.

8. The method of claim 6, wherein determining the second quality associated with the estimated vital sign of the person comprises:

providing the motion signal to a trained machine-learning model, wherein the trained machine learning model is trained on (1) a set of predetermined features associated with a set of motion signals, (2) a set of vital sign estimates, each vital sign estimates based on one of the motion signals in the set of motion signals, and (3) a ground-truth vital sign estimate, each ground-truth vital sign estimate corresponding in time with a vital sign estimate from the set of vital sign estimates; and receiving, from the trained machine learning model, a quality metric for the estimated vital sign of the person.

9. The method of claim 6, further comprising determining, based on a combination of at least one color feature of the color signal and at least one motion feature of the motion signal, a third quality associated with the vital sign estimate, wherein the third quality identifies a third accuracy of the rPPG-based estimate of the vital sign using at least a subset of the same plurality of images of the region of interest that is used to perform the rPPG-based estimate of the vital sign.

10. The method of claim 9, further comprising one or more of:

discarding, based on a comparison of the third quality with a corresponding threshold value, the vital sign estimate; or weighting, based on the comparison of the third quality with the corresponding threshold value, an rPPG signal associated with the vital sign estimate.

11. The method of claim 9, further comprising:

determining whether the third quality is below a corresponding threshold value;

when the third quality is below the corresponding threshold, then determining whether the second quality is below a second threshold;

when the second quality is below the second threshold, then providing a notification comprising an identification of the vital sign estimate as noisy due to one or more motion artifacts;

when the second quality is not below the second threshold, then determining whether the first quality is below a first threshold;

when the first quality is below the first threshold, then providing a notification comprising an identification of the vital sign estimate as noisy due to one or more light-based artifacts;

when the first quality is not below the first threshold, then providing a notification comprising an identification of the vital sign estimate as noisy.

12. The method of claim 6, further comprising:

accessing a window of rPPG data determined from the plurality of images;

stepping through the window of rPPG data with a predetermined step size and predetermined sub window size;

determining, for each sub window, an rPPG-based vital sign estimate corresponding to that sub window;

determining, based on the combination of at least one color feature of the color signal and at least one motion feature of the motion signal, a third quality associated with each vital sign estimate; and determining, based on each vital sign estimate and on the third quality associated with each estimate, a final estimate for the vital sign.

13. The method of claim 12, wherein determining, based on each rPPG-based vital sign estimate and on the third quality associated with each estimate, a final estimate for the vital sign comprises comparing each third quality with an associated quality threshold, wherein the value of the quality threshold depends on the sub window size.

14. One or more non-transitory computer readable storage media storing instructions and coupled to one or more processors that are operable to execute the instructions to:

capture, by a camera, a plurality of images of a region of interest of a person's skin;

access the plurality of images of the region of interest of the person's skin;

extract, from the plurality of images, a color signal of the region of interest as a function of time;

determine, based on the color signal of the region of interest extracted from the plurality of images, a remote photoplethysmography (rPPG)-based estimate of a vital sign of the person; and determine, based at least on the color signal, a first quality associated with the estimated vital sign of the person, wherein the first quality identifies an accuracy of the rPPG-based estimate of the vital sign using at least a subset of the same plurality of images of the region of interest that is used to perform the rPPG-based estimate of the vital sign.

15. The media of claim 14, wherein the instructions that when executed by one or more processors determine the first quality associated with the estimated vital sign of the person comprise instructions that when executed by one or more processors determine the first quality based on a set of predetermined, ranked features associated with the color signal and specific to the vital sign.

16. The media of claim 14, further comprising instructions that when executed by one or more processors cause the processors to:

extract, from the plurality of images, a motion signal of the region of interest as a function of time;

determine, based on the motion signal, a second quality associated with the estimated vital sign of the person, wherein the second quality identifies a second accuracy of the rPPG-based estimate of the vital sign using at least a subset of the same plurality of images of the region of interest that is used to perform the rPPG-based estimate of the vital sign.

17. The media of claim 16, further comprising instructions that when executed by one or more processors cause the processors to determine, based on a combination of at least one color feature of the color signal and at least one motion feature of the motion signal, a third quality associated with the vital sign estimate, wherein the third quality identifies a third accuracy of the rPPG-based estimate of the vital sign using at least a subset of the same plurality of images of the region of interest that is used to perform the rPPG-based estimate of the vital sign.

18. A system comprising:

one or more non-transitory computer readable storage media storing instructions; and one or more processors coupled to the non-transitory computer readable storage media, the one or more processors operable to execute the instructions to:

capture, by a camera, a plurality of images of a region of interest of a person's skin;

access the plurality of images of the region of interest of the person's skin;

extract, from the plurality of images, a color signal of the region of interest as a function of time;

determine, based on the color signal of the region of interest extracted from the plurality of images, a remote photoplethysmography (rPPG)-based estimate of a vital sign of the person; and determine, based at least on the color signal, a first quality associated with the estimated vital sign of the person, wherein the first quality identifies an accuracy of the rPPG-based estimate of the vital sign using at least a subset of the same plurality of images of the region of interest that is used to perform the rPPG-based estimate of the vital sign.

19. The system of claim 18, further comprising one or more processors that are operable to execute the instructions to:

extract, from the plurality of images, a motion signal of the region of interest as a function of time;

determine, based on the motion signal, a second quality associated with the estimated vital sign of the person, wherein the second quality identifies a second accuracy of the rPPG-based estimate of the vital sign using at least a subset of the same plurality of images of the region of interest that is used to perform the rPPG-based estimate of the vital sign.

20. The system of claim 18, further comprising one or more processors that are operable to execute the instructions to determine, based on a combination of at least one color feature of the color signal and at least one motion feature of the motion signal, a third quality associated with the vital sign estimate, wherein the third quality identifies a third accuracy of the rPPG-based estimate of the vital sign using at least a subset of the same plurality of images of the region of interest that is used to perform the rPPG-based estimate of the vital sign.

*    *    *    *    *